United States Patent [19]

Watanabe et al.

[11] Patent Number: 4,626,514

[45] Date of Patent: Dec. 2, 1986

[54] GOOD AESTHETIC ARTIFICIAL DENTAL MATERIALS BY CALCIUM PHOSPHATE GLASS-CERAMIC

[75] Inventors: Akira Watanabe, Okayama; Yoshimitsu Takeuchi, Bizen; Hiroyasu Tokuda, Bizen; Seiji Kihara, Bizen; Yasuhiro Makino, Bizen; Keiji Kamegawa, Bizen, all of Japan

[73] Assignee: Kyushu Refractories Co., Ltd., Okayama, Japan

[21] Appl. No.: 844,893

[22] Filed: Mar. 27, 1986

Related U.S. Application Data

[63] Continuation-in-part of Ser. No. 628,747, Jul. 9, 1984, abandoned.

[30] Foreign Application Priority Data

Jul. 8, 1983 [JP] Japan ................... 58-125164

[51] Int. Cl.$^4$ .............. A61C 13/08; C03C 10/02
[52] U.S. Cl. ........................... 501/10; 106/35; 433/203.1; 501/45; 501/46; 501/48; 501/73
[58] Field of Search ............... 501/10, 1, 27; 433/203; 106/35

[56] References Cited

U.S. PATENT DOCUMENTS

| | | | |
|---|---|---|---|
| 4,167,417 | 9/1979 | Franz et al. | 433/203 |
| 4,189,325 | 2/1980 | Barrett et al. | 433/203 |
| 4,309,485 | 1/1982 | Kondo | 428/457 |
| 4,366,253 | 12/1982 | Yagi | 501/10 |
| 4,417,912 | 11/1983 | Abe | 501/10 |

FOREIGN PATENT DOCUMENTS 55-11625  3/1980  Japan.

OTHER PUBLICATIONS

Stecher, P. G., *New Dental Materials*, 1980, pub'd by Noyes Data Corp., Park Ridge, N.J., p. 110.
Phillips, R. W., *Skinner's Science of Dental Materials*, 8th ed., 1983, pub. by W. B. Saunders & Co., Phila., p. 503.

*Primary Examiner*—Helen M. McCarthy
*Attorney, Agent, or Firm*—Koda and Androlia

[57] ABSTRACT

Dental materials using calcium phosphate glass-ceramics and having the color tone with high approximation to that of natural teeth. In those dental materials, calcium phosphate composite, nickel oxide and one or more other type of compounds selected from oxides of iron, manganese, cerium, titanium and tungsten, are contained as coloring component. Also, if necessary, $Al_2O_3$ and/or $SiO_2$ is contained as a color assisting agent in that composite. The calcium phosphate glass-ceramic according to this invention consists of the same components as that of natural teeth. Besides, it is possible to adjust the color tone delicately to match with the color tone of each individual's teeth. Moreover, the coloring components are incorporated in crystals of calcium phosphate. Consequently, they cause no elution during use and are therefore ideal as dental material.

2 Claims, No Drawings

GOOD AESTHETIC ARTIFICIAL DENTAL MATERIALS BY CALCIUM PHOSPHATE GLASS-CERAMIC

This is a continuation-in-part application of Ser. No. 628,747, filed July 9, 1984, now abandoned.

BACKGROUND OF THE INVENTION

1. Field of the Invention

This invention relates to dental materials made from calcium phosphate glass-ceramics having the color tone equivalent or close to that of natural teeth. The dental materials in this invention mean the materials used for crown inlays, bridges, etc. (hereinafter referred to simply as tooth-crown) and artificial teeth combining tooth-roots, implants, etc. (hereinafter called simply tooth-root) with the tooth-crowns.

2. Prior Art

Materials used conventionally for dental restoration of tooth-crowns, tooth-roots, etc. have been metals and plastics. However, these materials have the following defects. That is, they have seriously poor affinity with the living body, while such affinity is one of the most important characteristics required for medical material. Furthermore, depending on the condition of their use, metals or plastics are eluted, thus causing harmful effects to the living body. Recently, with the purpose of solving these problems, attempts are being made to use ceramic materials, such as alumina, for the foregoing dental materials. However, these ceramic materials are better than the former only in that they are not harmful to the living body, and they are also low in affinity to the living body.

As the materials which are free of the above-mentioned defects of various types of materials, calcium phosphate glass-ceramics are offered. These calcium phosphate glass-ceramic materials are ideal as dental materials in light of their characteristics as mentioned below. (1) As are natural teeth, these materials are composed primarily of phosphorus and calcium, and have a high affinity with gingival tissue. (2) Through crystallization, their strength is improved. Besides their hardness is almost the same as that of natural teeth. Therefore, mutual wear during chewing can be lowered (restricted). (3) During use, elution of the material components due to saliva, food, etc. is not caused, and even if it is caused, the eluted material components do not affect the human body at all because they are identical with the components of natural teeth. (4) Their melting points are similar to those of metallic materials. Accordingly, they can be cast by the lost wax process.

The disadvantages of such excellent calcium phosphate glass-ceramics are the whitish color tone and the inferior aesthetic appearance resulting from the difference in color tone from that of natural teeth.

In order to improve the aesthetic appearance, for metallic materials, facing processes are employed. These facing processes include the resin facing process to cover with acrylic hard resin, and the porcelain facing process to enamel with ceramic materials through baking. All of these processes, however, have the same shortcoming as that caused when the entire portion of artificial teeth-crown are made of resin or porcelain. Also, in the porcelain facing, when the aesthetic effect is particularly required, coating and baking processes must be repeated for three layers, i.e., the opaque layer, the dentin layer and the enamel layer. Accordingly, the time and cost for this process becomes enormous.

Therefore, it is preferable to color the starting materials themselves by adding coloring agents to the starting materials. However, the addition of pigments presents the possible danger that such pigments may harm the living body by eluting gradually during the use of the artificial teeth in which they are contained.

SUMMARY OF THE INVENTION

The present invention was completed after various studies conducted by the inventors with the foregoing facts in mind. The primary object of this invention is to provide dental materials using calcium phosphate system crystalline glass which are excellent aesthetically and thus ideal for preparing artificial teeth. The aesthetic effect involves the color tone as well as the transparency equal to or close to the color tone and transparency of natural teeth, with delicate adjustability allowed in the process of preparing such materials.

In keeping with the principles of this invention, the objects are achieved as follows. Into calcium phosphate system starting materials, coloring components are added. In some cases, in addition to those coloring components, coloring assistant agents are added. Then, the mixtures are processed to obtain fused glasses. These glasses are cast into forming tooth-crowns, combined bodies of tooth-crowns and tooth-roots, etc. Thereafter, the cast products are crystallized. At this point, the color tone of natural teeth is obtained. Furthermore, into the composites of the starting materials, rare earth compounds are added to effect the further improvement in strength as well as toughness of the calcium phosphate glass-ceramics.

In this invention, the color tone of natural teeth is not produced by the color of the coloring agents, but it is obtained by the reaction between the coloring agents and the components of calcium phosphate which are the starting material. Therefore, the desired color tone is obtained only after taking the processing steps of mixing, melting, casting, and crystallization. Besides, the dental materials provided by this invention do not just show the color tone of natural teeth, they also have the transparency of teeth. In addition, through controlling the conditions, such as the combination as well as the mixing ratio of the added coloring components, the content ratio of the coloring components compared with the starting materials, the color tone to be obtained can be adjusted delicately. Accordingly, the dental materials in accordance with this invention are characteristic in that they can be matched to the color tone of each individual's teeth as well as the color tone of each different tooth at different positions, such as a front tooth or molar.

DETAILED DESCRIPTION OF THE INVENTION

A detailed description will hereunder be given on dental materials obtained by using calcium phosphate glass-ceramics according to this invention.

Basic starting materials of calcium phosphate system used in this invention are compounds containing calcium, which produce CaO by calcination, and compounds containing phosphorus, which also give oxides of phosphorus, such as $P_2O_5$, by calcination. As calcium-containing compounds, calcium oxide, calcium hydroxide, calcium carbonate, calcium hydrogencarbonate, basic calcium carbonate, etc., and calcium salts of organic acids, such a calcium oxalate, calcium acetate, etc. may be used. As phosphorus-containing compounds, for example, orthophosphoric acid, metaphosphoric acid, and polyphosphoric acids, such as pyrophosphoric acid, triphosphoric acid, trimetaphosphoric acid, tetrametaphosphoric acid, or ammonium salts of these phosphoric acids, etc. may be used. Also, calcium salts of phosphoric acids, such as calcium hydrogenphosphate, calcium dihydrogenphosphate, calcium phosphate, calcium pyrophosphate, calcium polyphosphate, various apatites, may used as single compound or by mixing with the other calcium-containing compounds or phosphorus-containing compounds.

The ratio of calcium-containing compounds to phosphorus-containing compounds for use is 0.35–1.7, preferably 0.45–0.7, in atomic ratio of calcium to phosphorus Ca/P in those compounds. When the above-mentioned atomic ratio exceeds 1.7, the melting point becomes extremely high and vitrification does not occur. As a result, devitrification occurs during cooling. When devitrification occurs, coarse crystal grains of calcium phosphate are formed in the structure, thus inviting the undesirable outcome of seriously worsened brittleness as well as degraded toughness. On the other hand, when the atomic ratio is lowered to below 0.35, while the melting point gets lowered and vitrification becomes facilitated, it takes a long tome for the crystallization process, that will be mentioned later, with the additional undesirable outcome of chemical instability caused by liberation of phospheric acid.

The dental materials provided by this invention are characterized in that into the above-mentioned starting materials, nickel oxide and one or more other components, preferably one to two components, which are selected from the following compounds are added as coloring components. The compounds mentioned above are nickel oxide, those which contain iron, manganese, cerium, titanium and tungsten as coloring components for the foregoing starting materials, and which can be turned into oxides during the melting process that will be mentioned later. Such compounds are, for example, oxides, acetates, sulfides, nitrates, carbonates, and ammonium salts of the metals listed above.

When each of these coloring components is solely added to Ca/P glass, the colors which will appear after the crystallization are: skin color by NiO; white by $TiO_2$ and MnO; yellow by $CeO_2$; grey by $Fe_2O_3$; and blue by $WO_3$.

The color of natural teeth is very delicate. Not only the color tone but transparency and darkness of low brightness are also very important for the teeth, though these vary depending upon the individual.

The inventors studied the various combinations of these elements. It was found that NiO was an essential element and that the binary or ternary systems obtained by mixing one or more of the coloring components to NiO were very effective to accomplish the objects of the present invention. Further, when more than three components are mixed, very delicate color tones can be obtained. In any event, with 0.01–3.5% of NiO added to the coloring component(s) as a main element, a color which is very similar to natural teeth can be obtained.

Desired color tones can be obtained by mixing a nickel oxide component and one more component of those coloring components, with a specified ratio. When the color components are added, the hue varies depending on the combination and composition ratio of the components. Also, in the above-mentioned case, the shade (darkness) of the color varies depending on the adding ratio of the total amount of the coloring components. Table 1 shows examples of the preferable combination and composition ratio of the coloring components when the coloring components added are two to three in type.

The total amount of the coloring components added is 0.3 to 5 parts by weight (wt. pt.) compared with 100 wt. pt. of the calcium phosphate starting material, in calculation in terms of oxide. When the amount added is less than 0.3 wt. pt., the coloring is insufficient and the color is blocked by white color of calcium phosphate crystalline glass. On the other hand, when it exceeds 5 wt. pt., not only the coloring after crystallization becomes too dark, but also the melting point of the mixture gets higher and the viscosity of the melt increases, making it difficult to cast.

TABLE 1

|  | COMPONENT SYSTEM | COMPOSITION RATIO |
|---|---|---|
| BINARY SYSTEM | Fe—Ni | Fe 0.3–0.6, Ni 0.4–0.7 |
|  | T—Ni | Ti 0.5–0.8, Ni 0.2–0.5 |
|  | Mn—Ni | Mn 0.5–0.9, Ni 0.1–0.5 |
|  | W—Ni | W 0.4–0.85, Ni 0.15–0.6 |
| TERNARY SYSTEM | Fe—Mn—Ni | Fe 0.2–0.4, Mn 0.2–0.6, Ni 0.2–0.4 |
|  | Ce—Ti—Ni | Ce 0.2–0.5, Ti 0.2–0.7, Ni 0.1–0.3 |
|  | Fe—Ce—Ni | Fe 0.2–0.6, Ce 0.2–.04, Ni 0.2–0.4 |
|  | Fe—W—Ni | Fe 0.2–0.4, W 0.2–0.4, Ni 0.2–0.5 |

(Note)
The composition ratio is represented by the ratio by weight (wt. %) after converting into oxide (in oxide equivalent).
(Total amount of color components = 1)

As was mentioned above, the dental materials using calcium phosphate glass-ceramics provided by this invention are capable of giving the color tone close to that of natural teeth through the addition of the coloring components. Furthermore, through the still further addition of $Al_2O_3$ and/or $SiO_2$, the aesthetic appearance can be enhanced more. For such addition, in addition to oxides, hydroxides, hydroxy-carbonates; carbonates, nitrates, ammonium salts, etc. which become oxides during the melting process are used. These components act to facilitate the coloring at the time of the coloring through the reaction of the coloring components with the calcium phosphate components which are the starting material. The amount of such assisting components added is 10 wt. pt. or less, preferably 1 to 5 wt. pt., compared with 100 wt. pt. of calcium phosphate as the staring material according to the calculation conducted by converting oxides. When the amount added is more than 10 wt. pt., the result is undesirable because the viscosity of the melt becomes high and casting becomes difficult.

$Al_2O_3$ and/or $SiO_2$ added as a coloring assistant functions, in addition to as a coloring assistant, as a nucleus forming agent during the crystallization of calcium phosphate. Besides, they have the effect of inhibiting the growth of calcium phosphate crystal grains, and also they act to form a large amount of fine crystals. Therefore, the addition of such coloring assistant agents is still more desirable.

An example of the method for preparing the dental materials by calcium phosphate glass-ceramics according to this invention will be given below.

Calcium compounds, phosphate-containing compounds, and coloring component are weighed out, respectively, and mixed thoroughly. When necessary, the coloring assistant agent compound is also weighed out and mixed together with the foregoing components. If those components are in a solid state, they are pulverized before mixing. The mixture of starting materials thus obtained is placed in an appropriate vessel, and melted by heating to above 900 degrees centrigrade, preferably 1000 to 1600 degrees centigrade. For the vessel for melting, any quality of material may be used as far as it is hardly damaged (eroded) by the melt. Platinum is most desirable, but since it is high in price, alumina or zirconia vessels may be used although such vessels may suffer slight erosion to its internal surface. The melting temperature varies depending on the compounding ratio of the starting materials. However, when the above-mentioned range of temperature is used, the viscosity of the melt can be maintained sufficiently low. Thus, it is optimum for casting. When the melting temperature goes up, and particularly when it exceeds 1700 degrees centigrade, the phosphorus component starts to evaporate, and the composition changes gradually to have an excessive content of calcium, whereby pushing the melting point upward gradually. Accordingly, care should be taken in this regard. The melt mentioned above is cooled to a vitreous state. For cooling, any method may be used.

The vitreous material thus obtained is either cast-formed into dental material by using centrifugal casting process, pressure casting process, vacuum pressure casting process, etc. based on the lost wax process, or processed into specified form through compression molding after pulverizing into fine grains.

When the casting process is employed, the melting temperature used is above 900 degrees centigrade, preferably 1000 to 1600 degrees centigrade. The lost wax process is the method to be used for metallic materials. However, if the calcium phosphate used in this invention are 0.35-1.7 in the range of Ca/P, their melting point and viscosity are almost the same as those of metallic materials. Therefore, they are applicable to the casting by the lost wax process.

Because tooth-crowns, etc. thus obtained are glassy in state, they are processed for crystallization. The investment is heated in appropriate heating equipment, such as an electric furnace. The heating rate is 50°–400° C./hr, the heating temperature is 500–800 degrees centigrade, and the duration is 0.5-100 hr. Through this crystallization process, the coloring component reacted with calcium phosphate component is incorporated into crystals and stabilized. At the same time, it gives the color tone close to that of natural teeth.

The dental materials by calcium phosphate glass-ceramics in accordance with the present invention are characteristic in the following points in comparison with conventional dental materials.

1. They are the calcium phosphate materials which are ideal as dental material since their component materials and characteristics are similar to those of natural teeth, and their color tone is approximate to that of natural teeth, thereby contributing to improvement in aesthetic appearance.

2. Color tone can be varied through adjusting the type and quantity of coloring components, and it is possible to obtain the color that matches to each different individual.

3. The color components react with starting materials. Then, the coloring is effected as a result of this reaction, and at the same time, the coloring components become insoluble. Besides, the coloring components are incorporated in crystals. Accordingly, there is absolutely no possibility of occurrence of elution of the coloring components.

4. For the addition of the coloring components into the starting materials, exactly the same process as is used in ordinary case can be used. This further makes the use of complicated coloring process, as those used in porcelian facing, completely unnecessary.

5. Also, by further adding the coloring assistant agents, the aesthetic appearance can be improved still further.

Hereunder, the description will be given on this invention with reference to the embodiments.

EMBODIMENT 1

Fines of calcium carbonate and phosphoric acid were weighed out in a manner that the atomic ratio of calcium to phosphorus Ca/P becomes 1.0. Also, as coloring components, 1.0 wt% (out) of mixed powder of $CeO_2$ (40 wt%), $TiO_2$ (40 wt%), and NiO (20 wt%) was added. The mixture thus obtained was placed in a platinum crucible, and heated to 1250 degrees centigrade in an electric furnace, for melting by keeping it there for two hours. The melted material was poured into an alumina boat, and cooled. The sample at this time was a yellowish brown glass. This glass was again put in the electric furnace and heated to 620 degree centrigrade with a heating rate of 100° C./hr and maintained for 50 hours to compare its crystallization. The color tone after the crystallization was slightly grayish ivory, bearing close resemblance to the color tone of natural teeth. The Vickers hardness shown by the crystalized glass prepared as mentioned above was 432 kg/mm$^2$.

EMBODIMENT FOR COMPARISON 1

Crystallized glass was obtained by the same method as in EMBODIMENT 1, expect that the coloring components were not added. The product obtained this way was white in color, showing a great difference to the plate yellow color tone of natural teeth, and its Vickers hardness was 420 kg/mm$^2$.

EMBODIMENT FOR COMPARISON 2

Into calcium silicate glass powder, the coloring components (the same as in EMBODIMENT 1) were added to the same amounts, and the mixture was processed for crystallization after melting. However, the mixture was not crystalized, and it color tone was light blue.

EMBODIMENT FOR COMPARISON 3 ($CeO_2$-$TiO_2$ system)

Except that 1.0 wt.% of a mixture of $CeO_2$ (50 wt.%) and $TiO_2$ (50 wt.%) were added as the coloring component, the same coloring components as in EMBODIMENT FOR COMPARISON 2 were utilized. The resulting crystalline glass was pale yellow. The color is greatly different from the color of natural teeth.

EMBODIMENT 2

Calcium carbonate and phosphoric acid were weighed out by adjusting to obtain Ca/P (atomic ratio of calcium to phosphorus) equal to 1.0. As the coloring component, the mixed powder containing 30 wt.% of $Fe_2O_3$, 40 wt.% of $MnO_2$ and 30 wt.% of NiO was added in amount of 1.0 wt.% (out). Also, as the color assisting agent 1.0 wt.% of $Al_2O_3$ and 3.0 wt.% of $SiO_2$ (in wt.% out for both of them) were added. Then, the mixture of all of those components was melted, cast and crystallized under the same conditions as in EMBODIMENT 1. The color tone shown after crystallization was light ivory. When the composition ratio of the coloring components was changed to 40 wt.% in $Fe_2O_3$, 34 wt.% in $MnO_2$, and 29 wt.% in NiO, the color obtained became ivory tinted with increased yellow. Then, when the content ratio was further altered to 26 wt.% in $Fe_2O_3$, 34 wt.% $MnO_2$, and 40 wt.% NiO, a product with increased skin color was obtained. For both cases, the Vickers hardness was in the range of 400–432 $kg/mm^2$.

EMBODIMENT FOR COMPARISON 4
($Fe_2O_3$-$MnO_2$ system)

Crystalline glass was obtained in accordance with the same manner as Embodiment 2 except that 1.0 wt.% (out) of $Fe_2O_3$ (50 wt.%) and $MnO_2$ (50 wt.%) were added as coloring component. This glass was light yellow and was far different from the color of natural teeth.

As has been described above, through adding the coloring components and then processing with crystallization, the products obtained in accordance with this invention turned into ivory color from white color of calcium phosphate glass-ceramics along (EMBODIMENT FOR COMPARISON 1). This way, the products with the color tone close to that of natural teeth, and with physical properties, such as hardness, which are equal to those of natural teeth could be obtained. Also, it is known that the color shown by the products provided according to this invention result from the coloring unique to the calcium phosphate system starting materials, and it is not the color resulting from the direct coloring of the coloring components as they are and by themselves (EMBODIMENT FOR COMPARISON 2). Furthermore, the color of such product can be adjusted delicately as described in EMBODIMENT 2.

We claim:

1. Dental materials with calcium phosphate glass-ceramic consisting of:
   calcium phosphate composite with the atomic ratio of calcium to phosphorus Ca/P being 0.35–1.7; and
   a coloring component contained in said calcium phosphate composite, said coloring component being a mixture of nickel oxide and compounds selected from the group consisting of oxides of Fe, Mn, Ce, W, and Ti, the content of said coloring component is 0.3–5 wt. pt. against 100 wt. pt. of the calcium phosphate composite and the content of nickel oxide is 0.01–3.5 wt. pt. of said coloring component.

2. Dental materials with calcium phosphate glass-ceramic consisting of:
   calcium phospate composite with the atomic ratio of calcium to phosphorus Ca/P being 0.35–1.7;
   a coloring component contained in said calcium phosphate composite, said coloring component being a mixture of nickel oxide and compounds selected from the group consisting of oxides of Fe, Mn, Ce, W and Ti, the content of said coloring component is 0.3–5 wt. pt. against 100 wt. pt. of the calcium phosphate composite; and
   a color assisting agent being selected from the group consisting of $Al_2O_3$ and $SiO_2$, wherein the content of said color assisting agent is less than 10 wt. pt. against 100 wt. pt. of calcium phosphate composite.

* * * * *